US00RE37133E

(19) United States
(12) Reissued Patent
Maynard

(10) Patent Number: US RE37,133 E
(45) Date of Reissued Patent: Apr. 10, 2001

(54) METHOD OF PREPARING A BORATE ORGANIC COMPLEX ANION CONTAINING SALT COMPOSITIONS

(75) Inventor: Nigel P. Maynard, Auckland (NZ)

(73) Assignee: Fernz Timber Protection Limited, Auckland (NZ)

(21) Appl. No.: 08/912,374

(22) Filed: Aug. 18, 1997

Related U.S. Patent Documents

Reissue of:
(64) Patent No.: 5,221,758
Issued: Jun. 22, 1993
Appl. No.: 07/414,150
Filed: Sep. 28, 1989

U.S. Applications:

(63) Continuation of application No. 08/177,867, filed on Jan. 4, 1994, now abandoned.

(30) Foreign Application Priority Data

Sep. 28, 1988 (NZ) ..... 226377

(51) Int. Cl.[7] ..... C07F 5/02
(52) U.S. Cl. ..... 556/7; 548/110; 558/286; 558/288; 558/291; 558/293; 558/294
(58) Field of Search ..... 558/286, 288, 558/291, 293, 294; 556/7; 548/111

(56) References Cited

U.S. PATENT DOCUMENTS

| | | | | |
|---|---|---|---|---|
| 1,859,653 | * | 5/1932 | Craver et al. | 558/291 |
| 1,953,741 | * | 4/1934 | Bennett | 558/291 |
| 2,582,191 | * | 1/1952 | Curtis | 558/291 |
| 2,609,328 | * | 9/1952 | Reed | 426/62 |
| 2,710,252 | * | 6/1955 | Darling | 44/314 |
| 3,266,981 | * | 8/1966 | Stern et al. | 514/64 |
| 3,267,126 | * | 8/1966 | Weil | 558/290 |
| 3,373,170 | * | 3/1968 | Jones | 549/213 |
| 3,479,294 | | 11/1969 | Week | 252/182 |
| 3,702,241 | * | 11/1972 | Young | 504/193 |
| 3,860,626 | * | 1/1975 | Putnin et al. | 558/290 |
| 4,248,634 | * | 2/1981 | Forester | 106/15.05 |
| 4,742,044 | * | 5/1988 | Boden | 512/12 |

FOREIGN PATENT DOCUMENTS

| | | | |
|---|---|---|---|
| 42563/78 | | 12/1978 | (AU) . |
| 71716/87 | | 4/1987 | (AU) . |
| 15201/88 | | 3/1988 | (AU) . |
| 1077476 | * | 3/1960 | (DE) . |
| 1233875 | * | 2/1967 | (DE) . |
| 344702A1 | * | 7/1986 | (DE) . |
| 045 866 | | 2/1982 | (EP) . |
| 0115275 | * | 8/1984 | (EP) . |
| 600904 | * | 2/1926 | (FR) . |
| 971907 | * | 11/1960 | (GB) . |
| 916189 | * | 1/1963 | (GB) . |
| 1592011 | * | 7/1981 | (GB) . |
| 50012239 | | 7/1975 | (JP) . |
| 63-277601 | * | 11/1988 | (JP) . |
| PCT/AU90/00422 | | 5/1991 | (WO) . |

OTHER PUBLICATIONS

W. Kliegel, "Bor in Bologie, Medizin und Pharmazie", Sproinger–Verlag, Berlin, DE, pp. 163–167, 206–216, 370–395, 1980.*

Abstract from JP–A–50 012 239 (Kurray) Jun. 6, 1983/WPI, File Supplier, AN=75–41792W (25), Derwent Publications Ltd., London, GB, 1983.*

Chemical Abstracts, vol. 83 (1975) 92406b, Marine toxicant.

Chemical Abstracts, vol. 47(1953) 7141a, Reference to U.S. Pat. No. 2,609,328 (1952).

Chemical Abstracts, vol. 28, 3849–8, 1934, Reference to U.S. Pat. No. 1,953,741 (1934).

Chemical Abstracts, 1953, vol. 46, 9710a, Toxic effects of Boric Acid and its products with polyhydroxy–compounds, exptl.Path. Pharmakol. 207, 55–66 (1949).

*Chemical Abstracts,* vol. 10,1908,Preparation of sodium borosalicylate, Boll. Chim. Farm. 55, 263 (1916).

Chemical Abstracts, vol. 26, 3877, Reference to U.S. Pat. No. 1,859,653 (1932).

Chemical Abstracts, vol. 26, 7586a, Reference to U.S. Pat. No. 2,582,191 (1952).

Chemical Abstracts, 1959, vol. 53, 22229–22230.

Chemical Abstracts, vol. 74, 1971, 10685u, Oxytetracycline–glucose–yeast extract . . .

*Chemical Abstracts,* vol. 74, 1971, 10691t, Screening technique for estimating copper toxicity to estuarine phytoplankton.

*Chemical Abstracts,*vol. 54,23167d, Fungicidal Copper Compounds (1958).

*Chemical Abstracts,* vol. 67, 1967, 82984u, Tannin–boric complexes (1967).

*Chemical Abstracts,* vol. 57, 14060c,Inhibiting bacterial activity in petroleum (1962).

*Chemical Abstracts,* vol. 55, 11896b, Tanning andd fungicidal agents of tannin–boric acid compounds (1961).

*Chemical Abstracts,*vol. 66, 16900d, Reference to U.S. Pat. No. 3,266,981 (1966).

*Chemical Abstracts,* vol. 67, 1967, 53876e,Distributed ortho phenyl borates (1967).

* cited by examiner

*Primary Examiner*—Richard L. Raymond
(74) *Attorney, Agent, or Firm*—Jacobson, Price, Holman & Stern, PLLC

(57) ABSTRACT

A method of preparing a compound or formulation having biocidal or preservative properties, or both comprises reacting an organic complexing agent, preferably a selected organic alcohol, with a borate or boric acid to produce a borate organic complex ion. The complex ion is preferably further reacted with a suitable cationic species. A compound or formulation so prepared is also claimed.

10 Claims, No Drawings

METHOD OF PREPARING A BORATE ORGANIC COMPLEX ANION CONTAINING SALT COMPOSITIONS

Matter enclosed in heavy brackets [ ] appears in the original patent but forms no part of this reissue specification; matter printed in italics indicates the additions made by reissue.

*This is a continuation of application Ser. No. 08/177,867, filed Jan. 4, 1994, abandoned, which is a reissue of application Ser. No. 07/414,150, filed Sep. 28, 1989, U.S. Pat. No. 5,221,758.*

This invention relates to a compound, composition or formulation, and/or a method of preparing a compound or formulation, having biocidal properties against certain microbiological or macrobiological organisms, or both, for example, against certain fungi, insects and molluscs, and which is intended particularly though not necessarily solely for use in the preservation of timber.

It is therefore an object of the present invention to provide a biocidal and/or preservative compound, composition or formulation, and/or a method of preparing a biocidal and/or preservative compound, composition or formulation, which will at least provide the public with a useful choice.

Accordingly, in one aspect the invention consists in a method of preparing a compound or formulation having biocidal or preservative properties, or both, said method comprising the steps of:

reacting an organic complexing agent with a borate or boric acid to produce a borate organic complex ion.

Preferably, said method includes the further step of reacting said complex ion with a suitable cationic species.

Preferably said organic complexing agent is an organic alcohol.

Preferably said organic complexing agent is selected from the group consisting of 1,2 diols, 1,3 diols, 1,3,5 triols and polyhydroxy macrolide-type compounds.

More preferably said organic complexing agent is selected from the group consisting of naphthalene diols, phenyl glycols, glycerol ethers, dihydroxy phenyl compounds, dihydroxy anthracene compounds, methylol phenols, methylol naphthols, methylol anthrols, aliphatic 1,2 diols, aliphatic, 1,3 diols, and triol monoesters.

Preferably said cationic species is selected from the group consisting of ions of copper, zinc, hydrogen, barium, sodium, potassium, magnesium, calcium, iron, manganese, cobalt and nickel, and suitable cationic organic species, including alkyl ($C_9$–$C_{16}$) dimethyl amines, dialkyl ($C_7$–$C_{14}$) methyl amines, alkyl ($C_9$–$C_{16}$) dimethyl benzyl ammonium, dialkyl ($C_7$–$C_{14}$) dimethyl ammonium and substituted triazole compounds e.g. 1-[[2-(2,4-dichlorophenyl)-1,3-dioxolan-2-yl]methyl]-1N-1,2,4-triazole.

In a further aspect the invention consists in a compound, composition, or formulation having biocidal or preservative properties, or both, comprising the product of the method set forth in any of the preceding paragraphs.

In a still further aspect the invention consists in a compound, composition or formulation having biocidal or preservative properties, or both, comprising a borate organic complex ion.

Preferably said compound, composition, or formulation further contains a biocidally active cationic species.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

Presently preferred forms of the invention will now be described with reference to specific examples.

By way of example, one part of 2-chloro-4(1,1,3,3-tetra methyl butyl)-6-methylol-phenol was dissolved in three parts of kerosene and this solution is contacted and agitated for a short time (1 to 2 minutes) with an equal amount of aqueous solution containing 3% Borax. After agitation ceases the aqueous and organic phases separate. The organic layer can be analysed for Boron prior to use as, for example, a fungicide/insecticide in an organic solvent timber preservative. The aqueous layer can be replenished with further Borax prior to reuse.

The organic layer can be reacted further to produce biocidally more effective compounds for example as follows.

The organic layer is separated from the original aqueous layer, said organic layer being further contacted and agitated for a short time (1 to 2 minutes) with an aqueous solution containing 3% of a copper salt, for example, copper sulphate. The transfer of the copper cation to the organic phase can be followed by a darkening of colour of the organic phase.

After agitation ceases the aqueous and organic phases separate. The organic layer can be analysed for Copper and boron prior to use as a biocide.

Depending on the hydrophobicity of the diols and triols or polyhydroxy compounds used or the complexes formed one or a mixture of a range of solvents can be chosen. Examples of such solvents include white spirits, ketosene, chlorinated solvents (including Freons), aromatic esters, phosphate esters or alcohols (having 4 to 17 carbon atoms per molecule).

High capacity can be achieved at ambient temperatures, that is to say up to about 20% boric acid.

It has been shown that certain alcohols, e.g. 1-octanol, have a synergistic effect in preparation of the complexes when used as a co-solvent.

Thus boric acid and borates can be seen to form complexsalts stable to a greater or lesser degree, with organic alcohols. The alcohols are preferably 1,2 or 1,3 diols or 1,3,5 triols but can include polyhydroxy macrolide type compounds.

Possibly complexing agents include;

1. Naphthalene Diols

For example:

FORMULA I a)

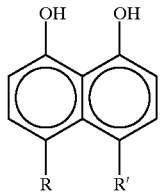

where R,R' are independently selected from the group consisting of hydrogen, halogen and aliphatic radicals of 1 to 8 carbon atoms;

FORMULA II b)

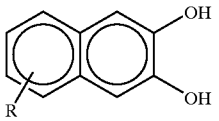

where $R^1$ is defined as R above;

2. Phenyl Glycols

For example:

FORMULA III a)

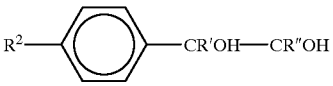

where R is selected from the group consisting of hydrogen, halogen and aliphatic radicals of 1 to 15 carbon atoms; and $R^{2'}$ is selected from the group consisting of hydrogen and aliphatic radicals of 1 to 8 carbon atoms and R" is selected from the group consisting of hydrogen, and aliphatic radicals of 1 to 8 carbon atoms, and phenyl substitutents;

FORMULA IV b)

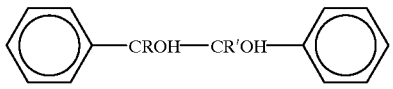

$R^3$ is selected from the group consisting of hydrogen and aliphatic radicals of 1 to 8 carbon atoms; and $R^{2'}$ is selected from the group consisting of hydrogen and aliphatic radicals of 1 to 8 carbon atoms.

3. Glycerol Ethers

For example:

a) $R—O—CH_2—CHOH—CH_2OH$ FORMULA V where $R^4$ is selected from the group consisting of saturated and unsaturated aliphatic radicals of 1 to 15 carbon atoms;

FORMULA VI b)

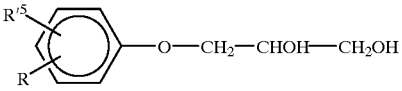

where R, $R^{3'}$ are independently selected from the group consisting of hydrogen, halogen, aliphatic radicals of 1 to 10 carbon atoms and halogen substituted aliphatic radicals of 1 to 10 carbon atoms.

4. Dihydroxy Phenyl Compounds

For example:

FORMULA VII

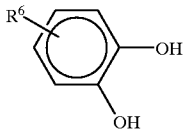

where R is an aliphatic radical of 1 to 15 carbon atoms, or is phenyl or cyclohexyl.

5. Dihydroxy Anthracene Compounds

For example:

FORMULA VIII

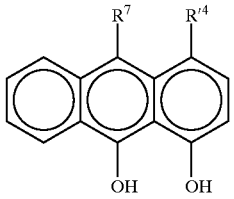

where $R^7$, $R^{4'}$ are independently selected from the group consisting of hydrogen, halogen and aliphatic radicals of 1 to 8 carbon atoms.

6. Methylol Phenols, Methylol Naphthols, Methylol Anthrols

For example:

FORMULA IX a)

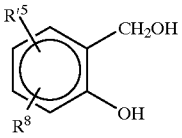

where $R^8$, $R^{5'}$ are independently selected from the group consisting of hydrogen, halogen, cyclopentyl, cyclohexyl, phenyl and aliphatic radicals of 1 to 15 carbon atoms;

FORMULA X b)

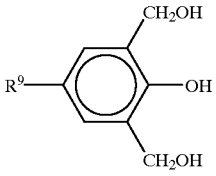

where $R^9$ is selected from the group consisting of aliphatic radicals of 1 to 15 carbon atoms, phenyl and cyclohexyl substituents;

FORMULA XI c)

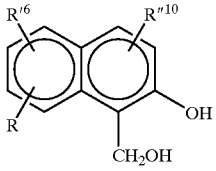

where $R^{10}$, $R^{6'}$, $R^{10''}$, are independently selected from the group consisting of hydrogen, halogen and aliphatic radicals of 1 to 8 carbon atoms;

FORMULA XII d) 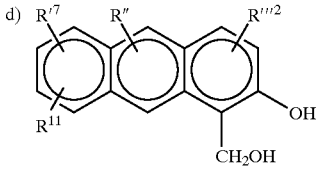

where R, R', R", $R^{2}$" are independently selected from the group consisting of hydrogen, halogen and aliphatic radicals of 1 to 8 carbon atoms.

7. Aliphatic 1,2 Diols

For example:

R—CR'OH—CR"OH—R'" FORMULA XIII where $R^{12}$, $R^{8'}$, $R^{3}$", $R^{1}$'" are independently selected from the group consisting of aliphatic radical of 1 to 8 carbon atoms, cyclohexyl and cyclopentyl substituents.

8. Aliphatic 1,3 Diols

For example:

R—CR'OH—$CH_2$—CR"OH—R'" FORMULA XIV where $R^{13}$, $R^{9'}$, $R^{4}$", $R^{2}$'" are independently selected aliphatic radicals of 1 to 8 carbon atoms.

9. Triol Monoesters

For example:

R—C—O—$CH_2$—CR'OH—CHR"—OH FORMULA XV where $R^{14}$, $R^{10'}$, $R^{5}$" are independently selected aliphatic radicals of 1 to 15 carbon atoms.

The preferred biocidally active cationic species is, for example copper or zinc but other cations such as hydrogen, barium, sodium, potassium, magnesium, calcium, iron, manganese, cobalt or nickel can be used. Also other suitable inorganic or organic species may be used. The species may be introduced by shaking the solvent containing the alkali metal organic complex boron salt in contact with an aqueous solution of, for example, a copper salt, for example, copper sulphate, so that the alkali metal for example sodium in the organic complex is replaced by copper ions.

Where the metal ion can be characterized as $M^{2+}$ then the complex could be

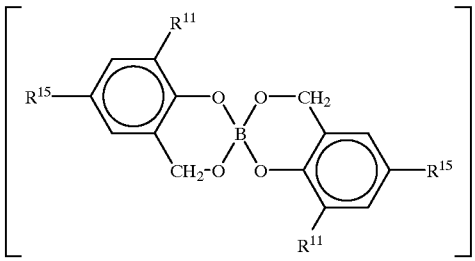

$M^{2-}$

-continued

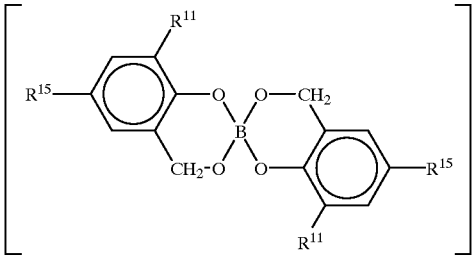

where $R^{11}$, $R^{11'}$ are independently selected from the group consisting of hydrogen, halogen, cyclopentyl, cyclohexyl, and phenyl substituents and aliphatic radicals of 1 to 15 carbon atoms.

Boron completes the octet of electrons in its outer shell by forming anionic complexes such as:

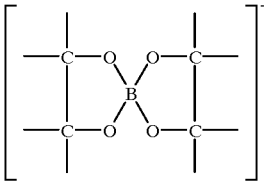

or

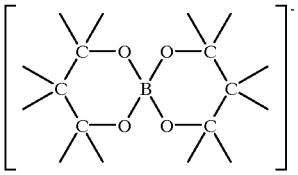

Many of the complexes described have very low solubility in water and therefore once distributed into for example a timber matrix should offer substantial resistance to leaching. An example of those with low solubility is a complex formed using the following diol:

FORMULA XVII

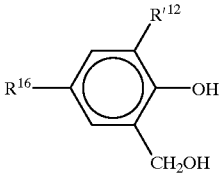

where $R^{16}$ is an aliphatic radical with 4 to 15 carbon atoms. $R'^{12}$ is halogen or an aliphatic radical with 1 to 15 carbon atoms.

The organic complex ion boron salts provided by the invention can be used for example to treat timber substantially in the known manners utilising vacuum pressure treatment or variations of this process or by diffusion into the timber.

In a further use the organic complex ion boron salt can be mixed with resins in solution or emulsion form to provide preservation of paint or to provide anti-fouling properties in marine paints or surface coatings for example to ships.

As a marine anti-fouling paint there would be little or no water contamination as copper and boron do not adversely effect sea water.

The organic complex ion boron salts may be used in agricultural applications to eliminate fungi, insects, molluscs or other organisms, which can restrict yields of produce.

Where aqueous carriers are preferred for a particular reason the complex ion boron salts may be utilised in the form of emulsions or micro emulsions which can be preferred for ease of handling or to reduce expense by using a cheaper carrying solvent.

By way of example, one commercially important area of use of the complex ion boron salts is in the area of timber preservation.

Many chemicals used in timber preservation of the present time are unacceptable for environmental reasons and restrictions are being applied to their use. These chemicals include arsenic, pentachlorophenol and tri butyl tin compounds. Boron chemicals can be used in some situations as a replacement for these chemicals but due to high aqueous solubility these boron compounds are also less suitable as they readily leach out of the timber, reducing efficacy.

The organic complex ion boron salts provided by the present invention are preferable since they have reduced solubility in water.

To illustrate the use in timber preservation, solutions of an organic complex ion boron salt and an organic complex ion boron salt containing copper were separately used to treat matched samples of *Pinus radiata* wood. Treated samples and control samples were exposed to several fungal species and also were placed in a fungal cellar in contact with contaminated soil. Comparisons with other known wood preservative fungicides showing improved efficacy are given in Table I.

TABLE I

| Toxic threshold values | | |
|---|---|---|
| | Preservative Toxic | |
| Fungus | Complex | Threshold % w/w |
| *Coriolus versicolor* | Boron + Copper | <0.03 |
| *Coriolus versicolor* | Boron only | 0.10–0.13 |
| *Coriolus versicolor* | TBTO | 0.025–0.05 |
| *Coniophora puteana* | Boron + Copper | 0.1–0.13 |
| *Coniophora puteana* | Boron only | 0.1–0.13 |
| *Coniophora puteana* | TBTO | 0.025–0.05 |
| *Gloeophyllum abietinium* | Copper + Boron | <0.03 |
| *Gloeophyllum abietinium* | Boron only | 0.06–0.1 |
| *Gloeophyllum abietinium* | TBTO | <0.025 |
| *Trametes lilacinogilva* | Boron + Copper | <0.03 |
| *Trametes lilacinogilva* | Boron only | 0.03–0.06 |
| *Trametes lilacinogilva* | TBTO | <0.025 |

Mean soundness figures after six months in a fungal cellar also showing the efficacy of the complexes, are given in Table II.

TABLE II

| | Retention % w/w | Soundness % |
|---|---|---|
| Copper + Boron | 0.08 | 94 |
| Boron only | 0.08 | 78 |
| TBTO | 0.08 | 78 |

Thus it can be seen that a method of treatment of timber and/or timber treated by such method are provided which have particular advantages.

Tests were carried out to determine efficacy against molluscs. Very weak solutions both in organic solvent and as an aqueous emulsion were applied to an inert surface (glass) and to plant surfaces and molluscs such as snails and slugs were encouraged to travel across the surfaces. In all cases sufficient biocide was assimilated to kill the molluses. It was also shown that at the concentration used the biocide was not phytotoxic to the plants.

There are many chemicals known in the art which have biocidal properties. However in certain end uses the choice of chemical is restricted by factors including high cost, environmental limitations or difficulties in formulating the compositions to obtain the physical properties required or desired for a particular end use.

Organic boron esters of the type

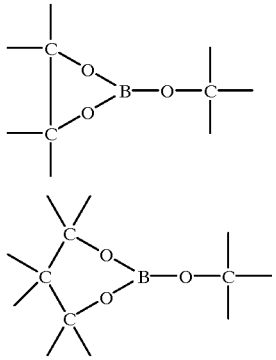

have been proposed as timber preservatives. These compounds are non ionic and are very sensitive to hydrolysis, releasing free boric acid which is easily leached reducing efficacy and usefulness in severe situations.

Boron compounds, which are relatively low in toxicity to humans but have good efficacy against lower forms of life, are incorporated into the compounds of the present invention, with the option of incorporating biocidally active cations as described hereinabove, copper, zinc, and other metallic cations and suitable including cationic organic species, in an organic complex ion salt, thus combining the benefits of the biocidally active components while obviating some or all of the disadvantages associated with earlier proposed formulations.

The present compounds have potential for use in many areas including replacement of, for example, tri butyl tin compounds in antifouling paints or timber preservatives, where said tin compounds are becoming environmentally unacceptable, and copper naphthenate in timber preservatives where the strong colour of the copper naphthenate may be a disadvantage. It is believed there is potential for use in preservation in wide ranging areas where insecticidal, fungicidal, molluscicidal, crustacacidal or the like properties are required.

What I claim is:

1. A method of preparing a salt composition having biocidal or preservative properties or both, comprising the steps of:

a) reacting an organic complexing agent selected from the group consisting of 1,2 diols, 1,3 diols, 1,3,5 triols and polyhydroxy macrolide-type compounds with borate or boric acid or both to produce a borate organic complex anion; and b) reacting said complex anion obtained in step a) with a biocidal cationic species [selected from the group consisting] of ions of copper [, zinc, barium, iron, manganese, cobalt, nickels, alkyl ($C_9$–$C_{16}$) dimethyl amines, dialkyl ($C_7$–$C_{14}$) methyl amines, alkyl ($C_9$–$C_{16}$) dimethyl benzyl ammonium, dialkyl ($C_7$–$C_{14}$) dimethyl ammonium and substituted triazole compounds] to form a neutral or partially neutralized salt.

2. The method of claim 1, wherein said organic complexing agent is selected from the group consisting of naphthalene diols, phenyl glycols, glycerol ethers, dihydroxy phenyl compounds, dihydroxy anthracene compounds, methylol phenols, methylol naphthols, methylol anthrols, aliphatic 1,2 diols, aliphatic 1,3 diols, and triol monoesters.

3. The method of claim 2, wherein the organic complexing agent is *a* methylol phenol.

[4. The method of claim 1, wherein said biocidal cationic species are selected from the group consisting of ions of copper, zinc and barium.]

[5. The method of claim 4, wherein said biocidal cationic species are ions of copper.]

6. The method of claim 1, further comprising the step of:

a1) dissolving wherein said organic complexing agent is dissolved in a solvent prior to step a), wherein said solvent is selected according to the hydrophobicity of at least said organic complexing agent or said borate organic complex ion.

7. The method of claim 6, wherein said solvent is selected from the group consisting of white spirits, kerosene, chlorinated solvents, aromatic esters, phosphate esters and alcohols having 4 to 27 carbon atoms per molecule.

8. The method of claim 6, wherein said organic complexing agent is dissolved in said solvent and a co-solvent.

9. The method of claim 8, wherein said co-solvent is 1-octanol.

10. A method of preparing a substantially water-insoluble composition having biocidal or preservative properties or both, comprising the steps of:

a) dissolving an organic complexing agent comprising 2-chloro-4-(1,1,3,3-tetra methyl butyl)-6-methylol-phenol in kerosene;

b) reacting said organic complexing agent obtained in step a) with a borate or boric acid or both to form a borate organic complex ion; and c) reacting said borate organic complex ion produced in step b) with an aqueous solution of a copper salt to produce said composition.

*11. The method of claim 2, wherein the organic complexing agent is a methylol naphthol.*

*12. The method of claim 2, wherein the organic complexing agent is a methylol anthrol.*

* * * * *